United States Patent [19]

Nolan et al.

[11] Patent Number: 6,004,274
[45] Date of Patent: Dec. 21, 1999

[54] METHOD AND APPARATUS FOR CONTINUOUS NON-INVASIVE MONITORING OF BLOOD PRESSURE PARAMETERS

[76] Inventors: James A. Nolan, 29805 Kennedy Gulch Rd., Conifer, Colo. 80433; Trevor J. Moody, 115 E. 34$^{th}$ St., No. 11C, New York, N.Y. 80016

[21] Appl. No.: 09/031,358

[22] Filed: Feb. 26, 1998

Related U.S. Application Data

[63] Continuation of application No. PCT/US96/14477, Sep. 10, 1996.
[60] Provisional application No. 60/003,682, Sep. 11, 1995.

[51] Int. Cl.$^6$ .................................................. A61N 5/00
[52] U.S. Cl. ............................................. 600/486; 600/481
[58] Field of Search .................................. 600/485, 486, 600/481, 479; D24/106; 607/136; 128/857

[56] References Cited

U.S. PATENT DOCUMENTS

| | | | |
|---|---|---|---|
| 4,928,692 | 5/1990 | Goodman et al. | 600/479 |
| 5,213,099 | 5/1993 | Tripp . | |
| 5,632,272 | 5/1997 | Diab et al. | 600/479 |
| 5,673,692 | 10/1997 | Schulze et al. | 600/479 |

FOREIGN PATENT DOCUMENTS

| | | |
|---|---|---|
| 0334652 | 9/1989 | European Pat. Off. . |
| 4226972-A1 | 2/1994 | Germany . |
| 404256727 | 9/1992 | Japan . |
| 405253194 | 10/1993 | Japan . |
| 406114018 | 4/1994 | Japan . |
| 406125882 | 5/1994 | Japan . |
| 232 444 | 6/1958 | U.S.S.R. . |
| 2162325 | 1/1986 | United Kingdom . |
| 2210168 | 6/1989 | United Kingdom . |
| 2284060 | 5/1995 | United Kingdom . |

*Primary Examiner*—Cary O'Connor
*Assistant Examiner*—Michael Astorino
*Attorney, Agent, or Firm*—Brian D. Smith, P.C.

[57] ABSTRACT

Continuous, non-invasive method and apparatus for measuring blood pressure parameters and the like are disclosed. One disclosed apparatus includes an earpiece for sealing an individual's ear canal so that arterial blood pressure changes adjacent the sealed ear canal produce air pressure changes in the sealed ear canal. The apparatus further includes pressure sensing means for measuring the air pressure changes in the sealed ear canal and producing a signal related to the measured air pressure changes. In addition, the apparatus preferably includes processing means for processing the signal to measure blood pressure parameters, as well as means for displaying and/or recording the processed signal. The method may be used to determine heart rate, blood pressure, cardiac output, stroke volume, cardiac function, circulatory function, and other parameters. To obtain absolute pressure readings, two sensors, one in each ear, may be used to monitor pulse time transit delay.

40 Claims, 5 Drawing Sheets

METHOD AND APPARATUS FOR CONTINUOUS NON-INVASIVE MONITORING OF BLOOD PRESSURE PARAMETERS

CROSS REFERENCE TO RELATED APPLICATIONS

This application is a continuation, claiming the benefit under 35 USC 365 (c), of PCT International Application No. PCT/US96/14477, filed on Sep. 10, 1996 which claims the benefit of U.S. provisional application Ser. No. 60/003,682, filed on Sep. 11, 1995.

TECHNICAL FIELD

The invention relates generally to method and apparatus for monitoring blood pressure and, more particularly, to non-invasive methods and apparatus for monitoring blood pressure and other blood pressure related parameters.

BACKGROUND OF THE INVENTION

The measurement of blood pressure is a well accepted procedure in many medical environments. These measurements typically comprise three parameters. The two most commonly used parameters are those referred to as systolic and diastolic pressure which are the maximum and minimum pressures, respectively, of the waveform. Mean arterial pressure is also used occasionally and provides an average reading of the pressure. In some situations, the continuous blood pressure waveform is also utilized. These measurements are often used for diagnosis of hypertension as well as general monitoring of patient status.

Apparatus for making these measurements fall into two basic categories, invasive and non-invasive devices. The most direct measurements are made by inserting an arterial catheter into the patient's artery. This method provides a very accurate measurement of blood pressure parameters and the blood pressure waveform at the site where the catheter is located. The pressure is measured in one of two ways. The original and most common method involves a thin cannula which provides a direct connection between the artery and a pressure measurement system. This method is attractive as it allows sampling of blood during operations and other procedures.

Another method utilizes a pressure transducer which is attached directly to the tip of the catheter with the signal transmitted electrically to the monitoring equipment. Despite the desirability of a direct blood pressure reading, this approach has a number of difficulties such as risk of infection, occlusion of the artery causing erroneous signals and serious artery damage, and risk of disconnection resulting in blood loss. As a result of these difficulties, arterial catheters are only used when absolutely necessary, for example, during major operating procedures and for some intensive care unit (ICU) patients where a continuous blood pressure signal for monitoring patient status is needed. Therefore, substantial opportunity exists for a non-invasive sensor that can provide a continuous blood pressure waveform.

Indirect blood pressure measurements are made with non-invasive sensors that may provide intermittent or continuous blood pressure measurements. Manual measurements are typically made through auscultation using a sphygmomanometer. This involves placing an occluding cuff around the patient's arm. The cuff is manually inflated using a separate bulb to a pressure which is sufficient to stop blood flow in the brachial artery. The operator uses a stethoscope to listen to the blood flow on the distal side of the cuff. The pressure in the cuff is slowly released. When the pressure in the cuff is equal to the systolic or maximum pressure, some blood will pass through the occluded artery. As this blood is forced through under pressure, squirting sounds known as Korotkoff sounds are produced which are heard through the stethoscope. By knowing the pressure in the cuff when the Korotkoff sounds are first heard, the systolic pressure can be derived. The pressure in the cuff is further reduced until the Korotkoff sounds disappear. This pressure is equivalent to the diastolic pressure since the artery is no longer being occluded.

While this method provides reasonably accurate systolic and diastolic measurements when used by an experienced operator, it is complicated to use. It also only provides intermittent readings of blood pressure and takes a lot of time to perform.

Numerous technologies exist to automate this measurement, the most popular of which are the automated auscultation and the oscillometric techniques. Automated auscultation is an automated version of the manual technique previously described. A microphone is placed underneath the cuff and an instrument senses the Korotoff sounds while inflating and deflating the cuff.

Oscillometry also uses an inflated occluding cuff but not the Korotkoff sounds. Instead, pressure sensors monitor the pressure inside the occluding cuff. When the pressure in the cuff is in between the systolic and diastolic arterial pressure, it partially occludes the blood flow and causes pressure changes in the artery to be transmitted into the cuff. Therefore, the onset and cessation of these pressure oscillations can be used to detect systolic and diastolic pressures respectively.

These techniques only provide intermittent readings of blood pressure parameters but take less time to conduct than the manual method using the sphygmomanometer. The accuracy of these products has also been questioned, particularly when the subject is moving. Motion drastically affects pressure in the cuff and, as such, affects the accuracy of the system. The accuracy of these methods has also been questioned when compared against direct measurements and manual auscultatory readings.

Several methods exist for the determination of continuous non-invasive blood pressure monitoring. However, none of these has been widely accepted. Problems include susceptibility to motion, questionable accuracy, and poor sensor locations.

Two recent methods include the finapres technology and arterial tonometry. The finapres method uses an active cuff attached to the patient's finger. The pressure in the cuff is adjusted by a servo mechanism so that it is equal to the arterial pressure. This can be achieved by keeping the volume of the artery fixed though a light source and a sensor transilluminating the finger. By maintaining this cuff pressure equal to the arterial pressure, a pressure transducer in the cuff provides a reading of the arterial pressure. While quite sophisticated, the accuracy of this method is susceptible to motion in the cuff which is a problem due to the fact that the finger is easily moved. Measurements made on the finger are also subject to substantial changes depending on the position of the finger relative to the heart and also to changes in the blood flow during changes in physiologic state.

Arterial tonometry places a piezoelectric film in close contact with the arteries in the wrist in order to monitor deflections in these arteries as a result of beat-to-beat changes in blood pressure. A piezoelectric film generates a voltage as a result of mechanical changes. By placing such a film in close contact with the arteries in the wrist, an electrical signal is generated that is representative of the arterial blood pressure waveform. This waveform is calibrated against an absolute measure of blood pressure to obtain systolic and diastolic readings from each cycle of the waveform. This method is also subject to inaccuracies due to motion and position of the arm, as well as questionable accuracy when compared against more accurate methods.

Many other technologies have been employed in an attempt to derive a continuous non-invasive blood pressure waveform. These include brachial artery stress-strain which monitors continuous pressure oscillations transmitted from the artery to a partially inflated cuff. Bioimpedance has also been used to monitor changes in the body's impedance as blood pressure changes. Finally, pulse time transit delay has been used to determine the difference in time of arrival of pressure waves at different sites in the body, for example, at the two ear lobes.

In a search for literature related to the subject matter of the present invention, the following documents were found, some of which disclose some of the aforementioned prior art methods. U.S. Pat. No. : 5,261,412 to Butterfield; U.S. Pat. No. 5,237,997 to Gruefbel; U.S. Pat. No. 5,163,438 to Gordon; U.S. Pat. No. 5,158,091 to Butterfield; U.S. Pat. No. 5,152,296 to Simons; U.S. Pat. No. 5,025,792 to Hon; U.S. Pat. No. 4,960,128 to Gordon; U.S. Pat. No. 4,846,189 to Sun; U.S. Pat. No. 4,807,638 to Sramek; U.S. Pat. No. 4,718,426 to Russell; U.S. Pat. No. 4,718,428 to Russell; U.S. Pat. No. 4,669,485 to Russell; U.S. Pat. No. 4,677,984 to Sramek; U.S. Pat. No. 4,425,920 to Bourland and U.S. Pat. No. 4,406,289 to Wesseling.

OTHER PUBLICATIONS:

de Jong et. al., Noninvasive Continuous Blood Pressure Measurement: A Clinical Evaluation of the Corotronic APM 770, Journal of Clinical Monitoring, Vol. 9 No. 1 January 1993.

Frucht U et. al., How reliable are indirect blood pressure measurement devices in the intensive care unit (ICU)? in Blood Pressure Measurements: New Techniques in Automatic and 24-hour Indirect Monitoring, Meywe-Sabellek W et. al. (eds.) Steinkopff Verlag Darmsstadt Springer-Verlag, New York 1990.

Latman NS, Evaluation of Finger Blood Pressure Monitoring Instruments, Biomedical Instrumentation and Technology, January/Feburary 1992, 26: 52–57.

Ramsey M, Automated Oscillometric Noninvasive Blood Pressure: Theory and Practice in Blood Pressure Measurements: New Techniques in Automatic and 24-hour Indirect Monitoring, Meywe-Sabellek W et. al. (eds.) Steinkopff Verlag Darmsstadt Springer-Verlag, New York 1990.

Siegel L et. al., Comparison of Arterial Tonometry with Radial Artery Catheter Measurements of Blood Pressure in Anesthetized Patients, Anesthesiology, V 81, No. 3, September 1994.

DISCLOSURE OF THE INVENTION

The present invention alleviates many of the problems associated with the aforementioned prior art systems for monitoring blood pressure with method and apparatus wherein the apparatus in its broadest sense includes an earpiece and measuring means cooperating with the earpiece for measuring arterial blood pressure changes adjacent the ear canal.

In a preferred embodiment the earpiece seals or includes means for sealing an individual's ear canal so that arterial blood pressure changes adjacent the sealed ear canal produce air pressure changes in the sealed ear canal. The measuring means of this preferred embodiment includes pressure sensing means for measuring or sensing the air pressure changes in the sealed ear canal. The measured or sensed air pressure changes (or the signals produced thereby) are then preferably processed to provide an indication of the individual's blood pressure and/or blood pressure related parameters. Such monitoring is made possible because air pressure changes in the sealed ear canal correspond to changes in the individual's blood pressure. The relationship occurs because the carotid artery (and perhaps other arteries as well) is in such proximity to the ear canal that blood pressure changes in the artery cause air pressure changes in the ear canal when it is sealed with an appropriate earpiece.

The above pressure sensing means preferably produces a signal related to the measured air pressure changes which may be displayed, recorded, or processed to monitor or measure an individual's blood pressure or blood pressure related parameters. For example, the signal may be processed to measure an individual's heart rate, systolic and diastolic pressure, mean arterial pressure, continuous blood pressure waveform, stroke volume, cardiac output, respiration rate and respiration volume.

In another preferred embodiment, the measuring means includes sensing means for measuring movement in the wall of an individual's ear canal which is caused by arterial blood pressure changes adjacent the ear canal. The sensing means of this embodiment preferably includes a strain gauge which is built into the earpiece so as to be capable of measuring movement transmitted through the earpiece from the wall of the individual's ear canal.

The method of the present invention for measuring blood pressure parameters and the like in its broadest sense includes the steps of wearing an earpiece such as that discussed above including means for measuring arterial blood pressure changes adjacent the ear canal and measuring the arterial blood pressure changes adjacent the ear canal with the earpiece.

In a preferred embodiment of the method, both ear canals of an individual are sealed so that arterial blood pressure changes adjacent each sealed ear canal produce air pressure changes in the adjacent ear canal. The method further includes the step of measuring the air pressure changes in each ear canal and producing a signal for each ear canal which is related to the measured air pressure changes. The signals of each ear canal are then compared to measure or monitor a blood pressure related parameter of the individual. In a preferred embodiment of this method, the time delay between the signals is measured which provides an indication of the individual's blood pressure.

BRIEF DESCRIPTION OF THE DRAWINGS

The invention will be more readily understood by reference to the accompanying drawings wherein like reference numerals indicate like elements throughout the drawing figures, and in which.

DETAILED DESCRIPTION OF THE PREFERRED EMBODIMENTS

Figure 1:
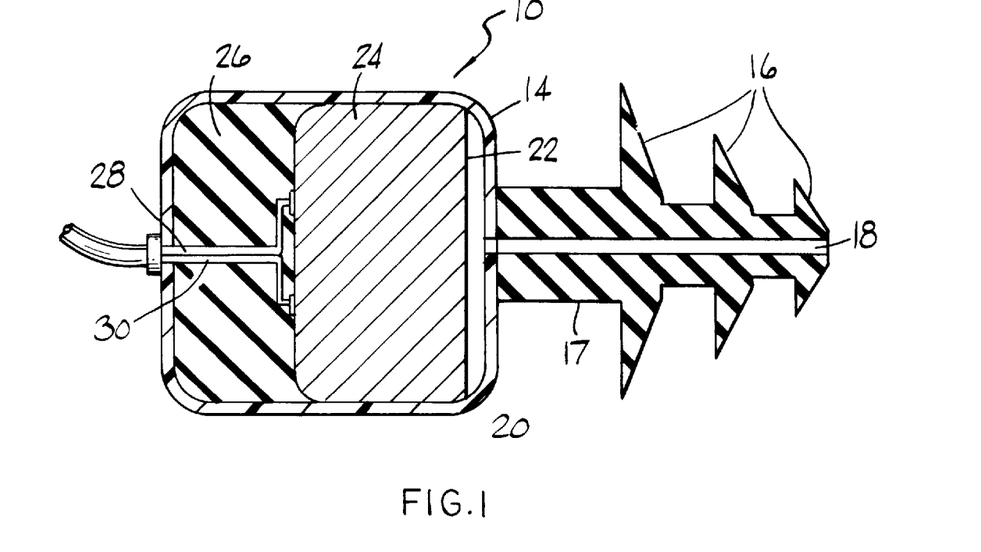
FIG. 1 is a cross sectional view of an earpiece of the present invention.
Figure 2:
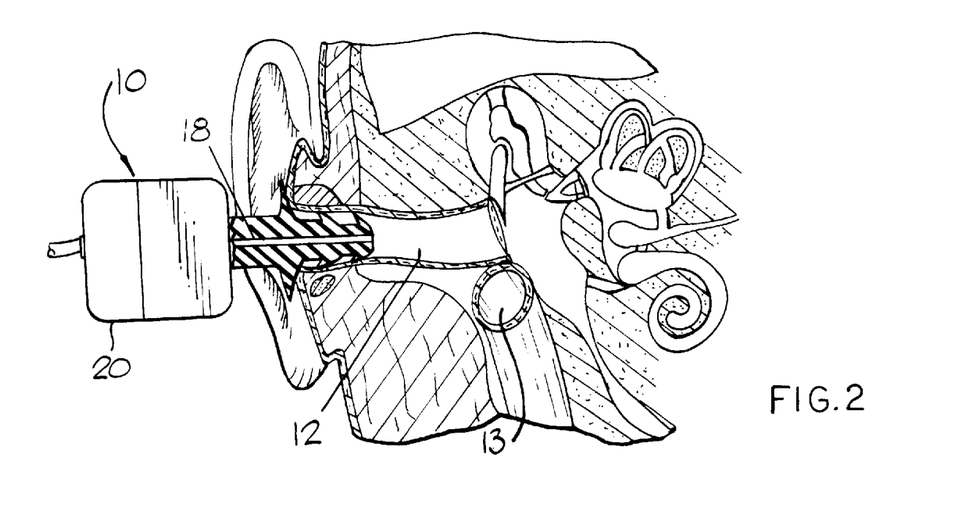
FIG. 2 is a partial cross sectional view showing the earpiece of FIG. 1 inserted into an individual's ear canal.

FIGS. 1 and 2 illustrate an earpiece 10 which is used to measure or monitor blood pressure and blood pressure related parameters in accordance with the present invention. FIG. 2 depicts earpiece 10 inserted into the ear canal 12 of an individual.

As best shown in FIG. 1, earpiece 10 has a molded rubber housing 14 which is provided with sealing ribs 16 on an end 17 thereof for sealing off an individual's ear canal, i.e. providing an air tight seal in an individual's ear canal when end 17 of the earpiece is inserted into an individual's ear, as such is shown in FIG. 2. A molded rubber housing which may be adapted for use as part of an earpiece 10 in accordance with the present invention is available under the trademark Norton Sonic II Hearing Protector from the North Specialty Products Company of Brea, California.

As also shown in FIGS. 1 and 2, molded housing 14 defines a pressure channel 18 which extends through end 17 of the earpiece to a main body portion 20 of the earpiece. When the earpiece is inserted in an individual's ear canal as illustrated in FIG. 2, pressure channel 18 will be in fluid, i.e. gaseous, communication with the ear canal 12, and with the surface 22 of a pressure sensing means or transducer 24.

Pressure transducer 24 is of a type in accordance with the present invention which is sensitive enough to detect pressure changes in an individual's (sealed) ear canal which are caused by the pulsing flow of blood though the arteries adjacent each ear canal, primarily the carotid artery which is generally located immediately below the ear canal. A pressure transducer which is believed to be sensitive enough to detect such pressure changes is a piezoelectric condenser microphone such as that manufactured and sold under the trademark Panasonic by Matsushita Electrical Corporation of America, Model Number 55A103.

As also shown in FIG. 1, the interior of body section 20 of the earpiece is filled with a rubber silicon fill 26 which helps support and maintain the position of pressure transducer 24 within body section 20. It will also be appreciated that pressure transducer 24 is electrically connected to signal processing means (not numbered), the details of which are shown and described in FIG. 3.

FIG. 2, as previously mentioned, illustrates earpiece 10 after it has been inserted in an individual's ear canal 12. FIG. 2 also illustrates that the individual's carotid artery 13 passes and is located directly beneath the individual's ear canal 12. Because of the carotid artery's proximity to the ear canal, blood pressure changes in this artery cause air pressure changes in the ear canal when the canal is sealed with an ear plug or earpiece such as earpiece 10. In addition, it has been found that these air pressure changes are directly related to the blood pressure changes. Accordingly, by monitoring or measuring the air pressure changes in the ear canal when it is sealed with an earpiece such as earpiece 10, one can directly monitor or measure an individuals' blood pressure and blood pressure related parameters.

Figure 4:
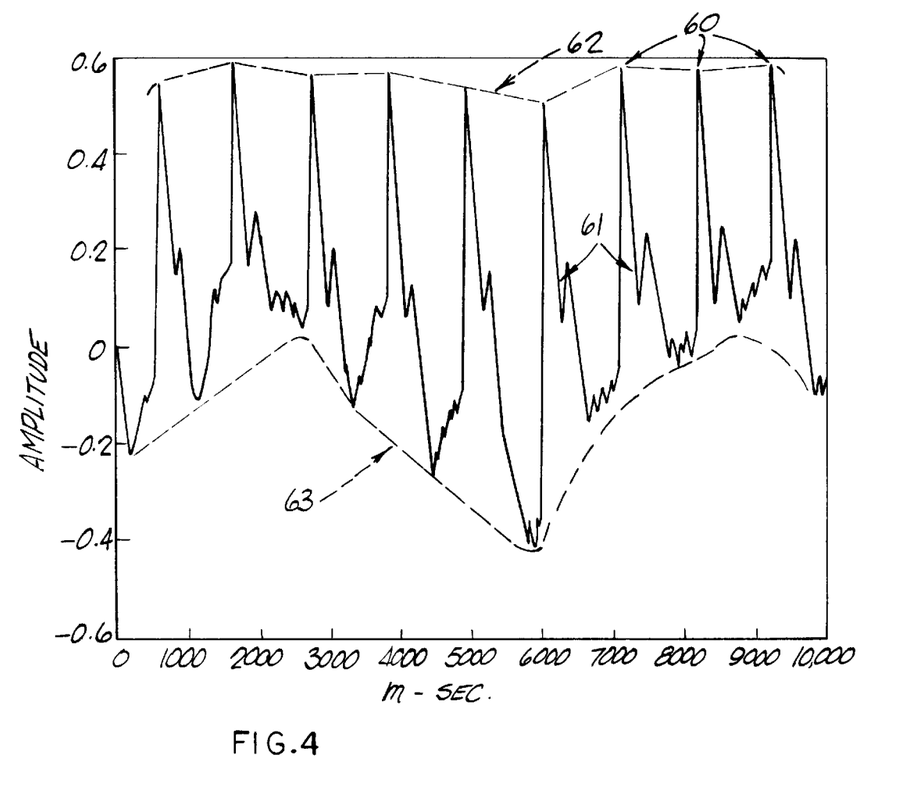
FIG. 4 is a graph illustrating the ear pressure changes occurring over a short period of time in an individual's ear canal which has been sealed with an earpiece of the present invention.

FIG. 4 shows a blood pressure waveform generated over a ten second interval with an earpiece 10 of the present invention sealing one ear canal of an individual. The amplitude of the waveform is normalized to dimensionless units with higher pressure indicated by the higher normalized ordinate value. The sharp peaks as indicated by 60 are the blood pressure peaks corresponding to each heart beat. The notches in the waveform indicated by 61 are abrupt changes in the arterial pressure due to valves closing in the heart and the reflection of blood pressure waves in the arterial system. The upper envelope 62 and the lower envelope 63 show the modulation of blood pressure by respiration. The amplitude of the lower envelope 63 is greater than that of upper envelope 62 because of the lower arterial pressure. The pressure changes due to respiration are a much larger percentage of the total pressure signal at lower pressures than at higher pressures.

Figure 5:
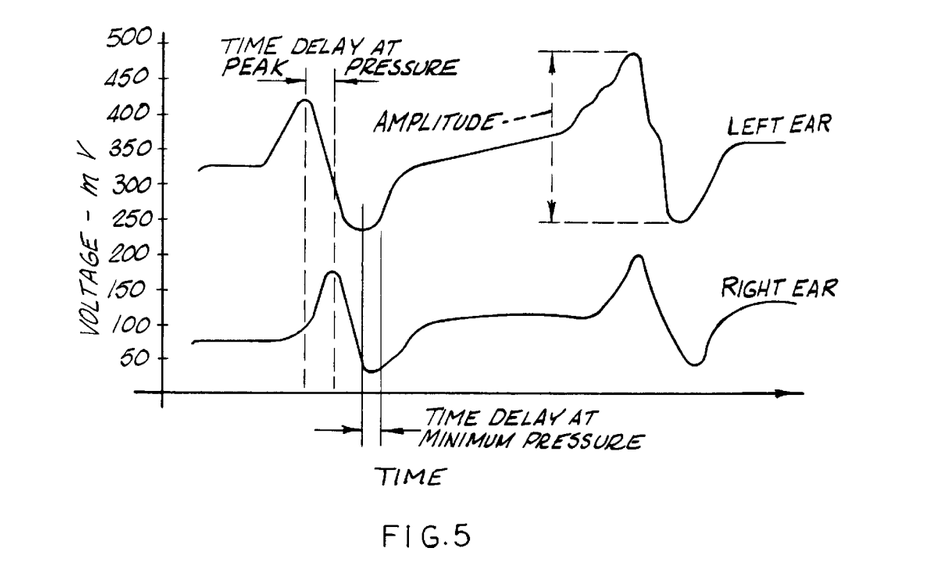
FIG. 5 is a graph illustrating the waveforms which are generated by insertion of an earpiece of the present invention in both of an individual's ear canals.

Additional information regarding an individual's circulatory system can be gained by sealing both of an individual's ear canals with an earpiece 10 of the present invention. FIG. 5 illustrates the waveforms which are generated by the insertion of an earpiece 10 in both ear canals. For ease of display, the waveforms are offset. The upper waveform, as illustrated in FIG. 5, is generated by the signal produced in the left ear, whereas the lower waveform is generated by the right ear. As illustrated, there is a time delay between the right and left ear waveforms as shown at the bottom of FIG. 5 which is caused by the fact that it takes slightly longer for blood to travel from an individual's heart to the carotid artery adjacent the right ear than to that adjacent the left ear. It has been found that by analyzing the time delay, information regarding an individual's circulatory function can be gained. For example, the time delay can be used to determine peak blood pressure, minimum blood pressure and continuous blood pressure.

Figure 3:
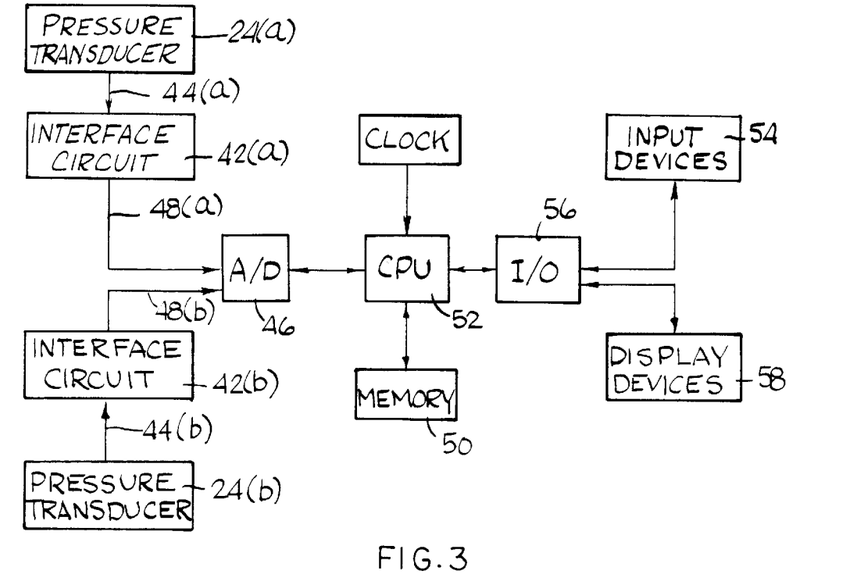
FIG. 3 is a block diagram illustrating implementation of the present invention in both of an individual's ears.

FIG. 3 is a block diagram illustrating implementation of the present invention in both of an individual's ears. As shown, a pair of pressure transducers 24(a) and 24(b), one for each ear, are inserted into an individual's ear canals (via a pair of earpieces 10 as previously described) to form a pressure tight seal in each ear canal. The blood pressure pulses in the arteries adjacent each ear canal, primarily the carotid artery, deform the adjacent sealed ear canal causing air pressure changes within the ear canal which are measured by one of the pressure transducers 24(*a*) and 24(*b*). The pressure signal from the pressure transducer is transmitted to an interface circuit 42(*a*) or 42(*b*) via a wire connection 44(*a*) or 44(*b*). The interface circuit 42(*a*) or 42(*b*) converts the pressure signal of the pressure transducer to an electrical signal that is compatible with the analog/digital (A/D) convertor 46. The electrical signal from the interface circuit is routed to the A/D convertor by two wire connections 48(*a*) or 48(*b*). The wire connections 48(*a*) and 48(*b*) each provide a signal line and ground line to the pressure transducer. The A/D convertor 46 converts the analog electrical pressure signals from interface circuits 42(*a*), (*b*) to discrete digital signals that can be stored in memory 50 and or processed by the central processing unit (CPU) 52. The conversion rate of pressure signals by the A/D convertor 46 must be fast enough to capture rapid changes of the pressure waveforms and not so fast that much of discrete digital signals are redundant. By the Nyquist sampling theorem, the minimum conversion rate necessary is one half the period of the highest frequency contained in the pressure waveform. The converted signal from the A/D 46 is stored in memory 50 where it can be displayed or processed at a later time.

CPU 52 controls the timing of the A/D 46, stores the digitized pressure waveform in memory 50, reads the input information from the input devices 54 through the I/O circuit 56 and outputs information through the I/O circuit 56 to the display devices 58. The input devices 54 can be such things as switches to turn on the blood pressure monitor and activate other functions, a keyboard input to control or select various functions of the monitor, or an analog or digital calibration input signal or numerical entry to calibrate the measured pressure waveforms against known blood pressure standards. The display devices can be such things as a computer monitor or cathode ray tube, a numerical display, a strip chart, a bar graph, a printer or an alarm indicator.

CPU 52 also processes the digitized pressure waveforms to filter out motion artifacts and noise in the pressure waveforms. In addition, CPU 52 processes the waveforms to determine blood pressure and related parameters by measuring the continuous time delay between the digitized pressure waveforms or by measuring the amplitudes of one or both of the digitized waveforms. The type of processing and display are selectable by the input devices 54 and the output is displayed on one of the display devices 58. The CPU 52 can also process the digitized pressure waveforms and determine alarm conditions such as high or low blood pressure, loss of signal and activate an alarm indicator in the group of display devices 58.

As previously mentioned, a suitable pressure transducer for use in the present invention is the aforementioned piezoelectric condenser microphone, Panasonic model number WM-55A103. Other pressure transducers which may be suitable for use in sensing pressure changes within an individual's sealed ear canal include piezoelectric transducers, coil magnet microphones, strain gauges and ceramic transducers.

Figure 7:
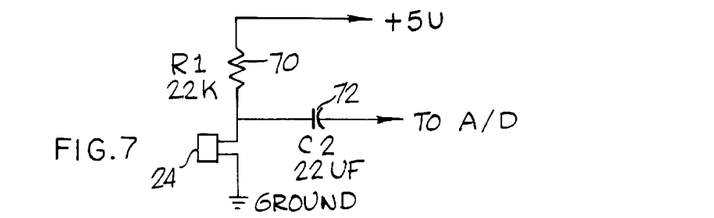
FIG. 7 is an electrical schematic showing the components of the interface circuit of FIG. 3.

A suitable interface circuit 42 for use in the present invention is housed in the Data Translations A/D Panel DT783 available from Data Translations of Mass. As shown in FIG. 7, the DT783 provides a 5 volt line (not numbered) which is connected to one of two electrodes (not numbered) of pressure sensor 24 through a 2.2 kilo ohm resistor 70. The pressure sensor side of resistor 70 is connected to the A/D input via a 22 uF capacitor 72. The remaining electrode (not numbered) of the pressure sensor is connected to ground.

A suitable A/D converter 46 for use in the present invention is available from Data Translation of Mass., Model No. DT-7101. A suitable CPU for use in the present invention is an 80486-DX available from the Intel Corporation of California. A suitable memory for use in the present invention is a 350 MB hard disk available from the Seagate Company of California. Components 50, 52, 54, 56 and 58 are all conveniently housed within many conventional microcomputers such as that available from Toshiba Corporation, Model No. T2100.

Figure 6:
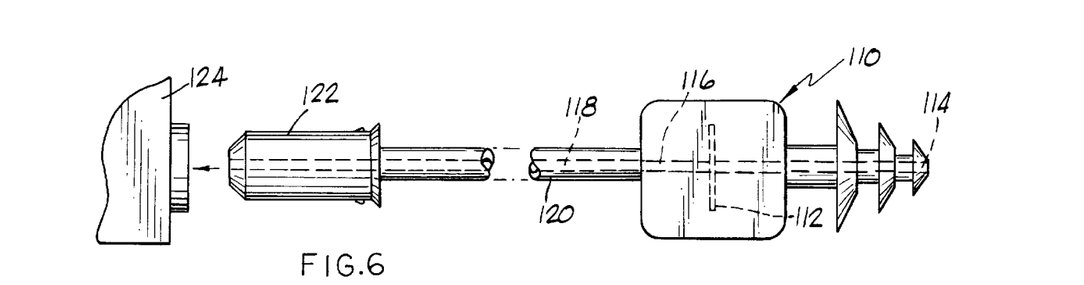
FIG. 6 is a partially broken away side elevational view of another embodiment of the present invention utilizing an earpiece for monitoring an individual's blood pressure related parameters.

FIG. 6 illustrates another embodiment of the present invention utilizing an earpiece 110 which is provided with a diaphragm assembly 112 instead of a pressure transducer 24 in the earpiece itself. As shown, the earpiece defines an air channel 114 which will be in fluid communication with an individual's ear canal when earpiece 110 is inserted into an individual's ear. When so inserted, the ear canal will also be in fluid communication with diaphragm assembly 112. As also shown, the other side of diaphragm assembly 112 is in fluid communication with another air channel 116 defined by a rear portion (not numbered) of earpiece 110 which in turn is in fluid communication with another air pressure channel 118 defined by a tube 120 which extends from earpiece 110 to a plug 122. As indicated, plug 122 is plugged into a test instrument 124 when it is desired to use the earpiece to measure or monitor an individual's blood pressure. Test instrument 124 contains a pressure transducer such as pressure transducer 24 of the previous embodiment for generating a signal which can be displayed, recorded, or otherwise processed. While it is believed that an ear plug or earpiece having a pressure transducer mounted within the earpiece itself will generally be preferable to that illustrated in FIG. 6, there may be applications where an earpiece such as that illustrated in FIG. 6 would be preferable.

Figure 8:
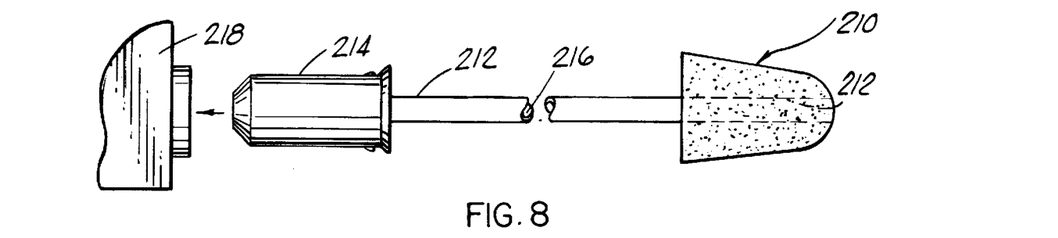
FIG. 8 is a partially broken away side elevational view of another embodiment of the present invention utilizing an earpiece for monitoring an individual's blood pressure related parameters.

FIG. 8 illustrates yet another embodiment of the present invention utilizing a closed cell foam-like earpiece 210 which as will be appreciated is not provided with a either a diaphragm assembly 112 or a pressure transducer 24 such as that provided in earpieces 10, 110. As shown, earpiece 210 has a flexible tube 212 extending through it and projecting out of it which connects to and extends through a plug 214. Tube 212 defines an air channel 216 which places an individual's ear canal in direct fluid communication with a test instrument 218 when earpiece 210 is inserted into an individual's ear. Test instrument 218 would contain a pressure transducer such as pressure transducer 24 or similar means for generating a signal for monitoring blood pressure and the like which can be displayed, recorded, or otherwise processed as described earlier. Closed cell foam is preferred for use in this embodiment and perhaps the other embodiments as well because it is believed to reduce motion artifacts in the signals generated which are caused by movement of the individual using the earpiece. A closed cell foam material suitable for use in earpiece 210 is sold under the trademark Ensolite and is available from the 3M Corporation Co. of Minneapolis, Minn.

Figure 9:
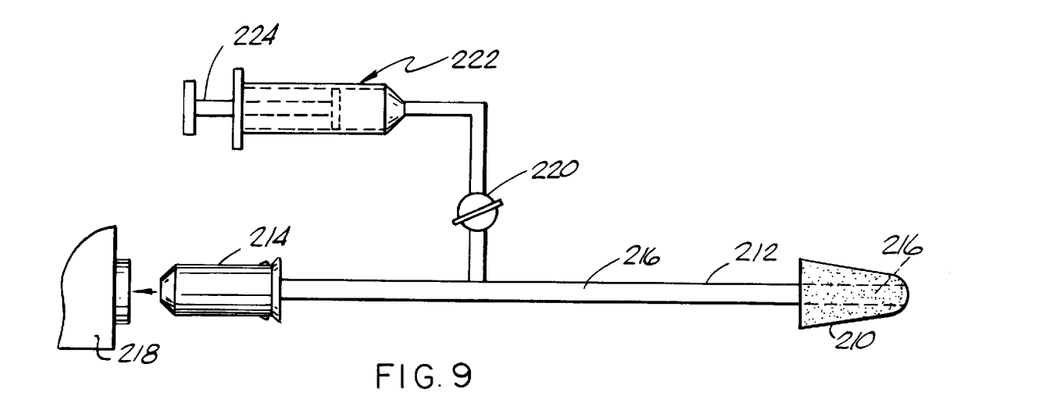
FIG. 9 is a side elevational view of an embodiment similar to that of FIG. 8 which is additionally provided with means for adjusting air pressure within the air channel of the system.

FIG. 9 illustrates another embodiment of the present invention which is similar to that of FIG. 8 and numbered similarly but additionally provided with means (not numbered) for controlling air pressure within flexible tube 212. As shown, the air pressure control means includes a pet cock valve 220 for controlling the flow of air into a syringe-like device 222 having a plunger 224. As those skilled in the relevant art will appreciate, one can adjust the air pressure within tube 212 after earpiece 210 is sealingly inserted in an individual's ear canal by moving plunger 224 within the syringe 222 to a position providing the desired air pressure. Regulating the air pressure within tube 212, i.e. in air channel 216, may be desirable in some situations where it is desirable or necessary for calibrating the signal being generated or bringing the pressure back to its baseline level if it happen to change. For example, pressure could go negative if the earpiece were inadvertently pushed farther into the ear canal which might create a partial vacuum in the air channel. The manual syringe/petcock system illustrated herein is merely one way of adjusting the pressure. Other more sophisticated means such as automatic means for enabling such which are known to those skilled in the relevant art are also contemplated and are considered to be within the scope of the present invention.

Figure 10:
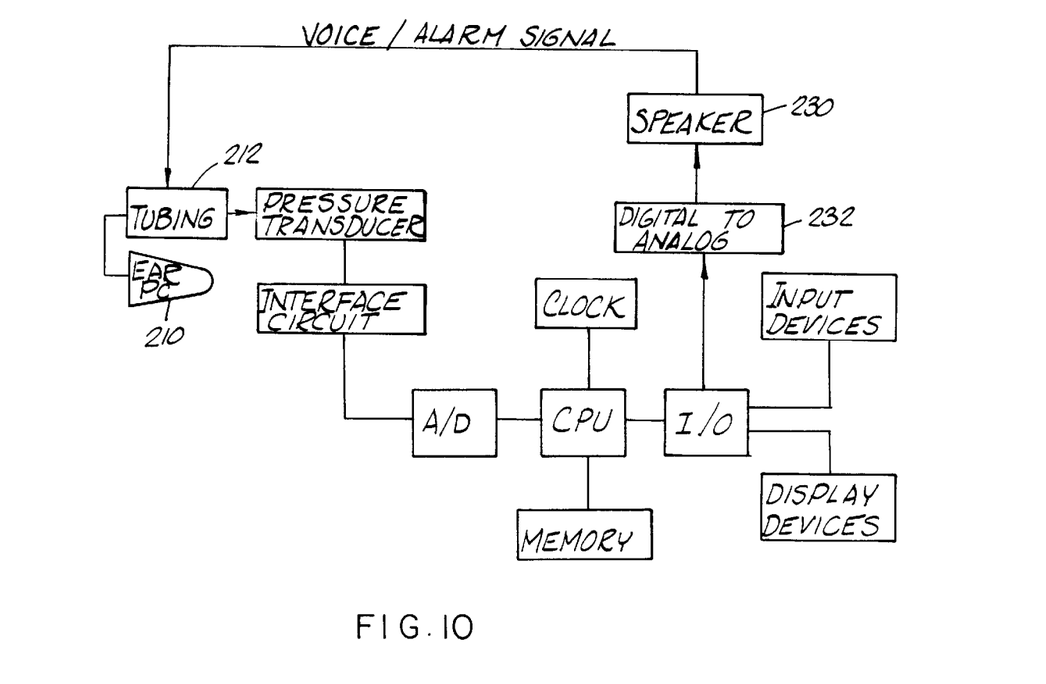
FIG. 10 is a block diagram illustrating yet another embodiment of the present invention which is additionally provided with means for generating an audio signal within the air channel of the system.

FIG. 10 schematically illustrates yet another embodiment of the present invention which is also similar to that of FIG. 8 and numbered similarly but additionally provided with means (not numbered) for generating an audio signal which is to be heard by the wearer of the earpiece. The audio signal could be an alarm, physiological information or music and could be provided in the form of a voice or a combination of tones. The audio signal is generated by a speaker 230 which is fluidly coupled to tubing 212 so as to direct the audio signal, i.e. sound generated by the speaker, into the air channel 216 of the tubing. The electrical signal sent to the speaker for generating the audio signal is preferably generated by a digital to analog converter 232 under control of the CPU. The circuitry for this embodiment is similar to that described in FIG. 3. However, FIG. 10 additionally illustrates the foregoing means for generating the audio signal. It will also be appreciated that the reference to two channel measurements and time delays is omitted in FIG. 10.

Figure 11:
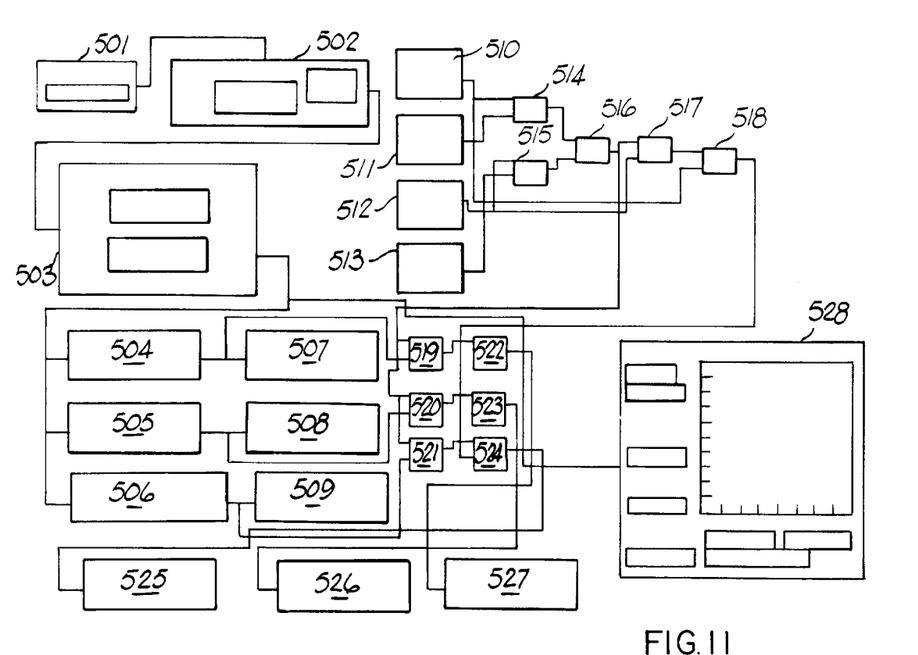
FIG. 11 is a block diagram of the developmental software that was used to control the hardware of FIGS. 3 and 10.

FIG. 11 is a block diagram of the developmental software that was used to control the hardware such as the CPU, memory, clock, I/O, A/D, display devices and input devices as shown in FIGS. 3 and 10. In addition, the software is used to calibrate the measured waveform against an external reference such as a cuff or catheter. The software is a commercially available data acquisition package which is available from Data Translations of Marlborough, Mass. and identified as DT VEE software. The software is used in a Toshiba notebook 2105CS computer with a Data Translations DT 7101 PCMCIA analog to digital converter card and a Data Translations interface box, model DT783. The notebook computer integrates the functions of CPU, clock, memory, I/O, input devices and display devices as shown in FIGS. 3 and 10.

The software is a graphical programming language, where functions appear as entire blocks. Blocks can be used for controlling a peripheral device, doing mathematical functions, displaying data and the like. The blocks have one or more inputs and outputs and the signal flow is represented by connecting lines.

Block 502 is the configuration panel for the A/D card. The total number of samples, sample rate and input voltage range for the A/D card are entered through this panel. Block 501 is a counter that sets the number of times that block 502 repeats its process. Block 503 takes the data from the A/D card and enters it into the computer. Through block 503 the channel of the A/D is selected as well as the number of sample points to be transferred from the A/D.

The output of block 503 is raw numerical data that is the voltage measured by the A/D converter. After this point the data is processed to show maximum voltage, minimum voltage and mean voltage. Block 504 reads the maximum voltage of the output of block 503 and displays it in block 507. Block 505 reads the minimum voltage and displays it in block 508. Block 506 reads the mean voltage and displays it in block 509.

The output of block 503 also goes to the real time graph block 528, where the measured pressure voltage is displayed vertically with time as the horizontal axis. In the display shown, voltage ranges from 0 to 5 volts with time ranging from 0 to 4 seconds.

The calibration of blood pressure to voltage is a linear type calibration that accounts for slope and offset. The calibration blood pressure that is measured with a standard sphygmomanometer (cuff) is entered in block 510 (high pressure reading) and block 511 (low pressure reading). The corresponding high and low voltage readings for the waveform are entered in blocks 512 and 513 respectively. The difference between the high and low pressure is calculated in block 514. The difference between maximum and minimum voltage is calculated in block 515. In block 516, the output of block 515 is divided into the output of block 514. The output of block 516 is the slope of the conversion formula for converting volts to pressure. The units of the output of block 516 are mmHg (millimeters of mercury pressure) per volt.

Block 517 multiplies the slope (from block 516) by the maximum blood pressure. This output of block 517 then has the maximum pressure subtracted from it in block 518, which gives the offset calibration. The slope and offset calibration are used to convert the voltages obtained from block 503 to pressure values.

The maximum voltage from block 504 is multiplied by the slope calibration in block 519. The minimum voltage from block 505 is multiplied by the slope calibration in block 520. The mean voltage is multiplied by the slope calibration in block 526. The offset calibration is subtracted from the outputs of blocks 519, 520, 521 in blocks 522, 523 and 524. The outputs of blocks 522, 523, 524 are the maximum, minimum and mean blood pressure in mmHg. The pressures are displayed in blocks 525 (mean), 526 (minimum) and 527 (maximum).

The operation of the software is a follows. The earpiece is inserted in the patients ear and a cuff is applied to the arm. The cuff readings are taken while the noninvasive waveform is recorded. The program is then stopped from recording and the cuff minimum, maximum pressures and the waveform minimum and maximum voltages are entered into the blocks 510, 511, 512, and 513. The cuff then can be removed from the patient. The software is then activated to record and measure the voltage pressure waveforms and display the patient's now calibrated blood pressure in blocks 525, 526, and 527.

Figure 12:
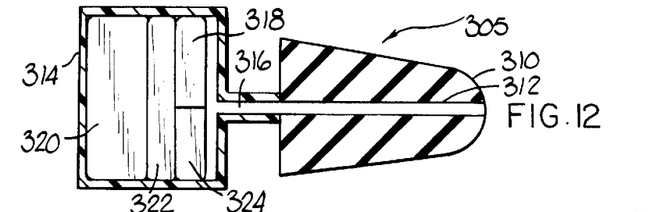
FIG. 12 is a cross sectional view of yet another embodiment of the present invention in which all components of the system are built into a device which can be worn by a subject.

FIG. 12 illustrates yet another embodiment of the present invention which is a completely self-contained device 305. As shown, device 305 preferably utilizes a closed cell foam-like earpiece 310 which is similar to earpiece 210. Earpiece 310 also has a tube 312 extending through it and projecting out of it which connects to a housing 314 for the electronics. Tube 312 defines an air channel 316 which places an individual's ear canal in direct fluid communication with a pressure transducer 318 contained within housing 314. Pressure transducer 318 would be similar to pressure transducer 24 for generating a signal in response to the pressures changes in the ear canal sealed by earpiece 310. Self-contained device 305 is preferably powered by a battery 320 which supplies power to the device's electronic circuitry 322 which is preferably similar to that illustrated in FIG. 10. As such, device 305 preferably has a speaker 324 similar to speaker 230 for generating an audio signal which is to be heard by the wearer of the earpiece. As with the embodiment of FIG. 10, the audio signal could be an alarm, physiological information or music and could be provided in the form of a voice or a combination of tones.

Figure 13:
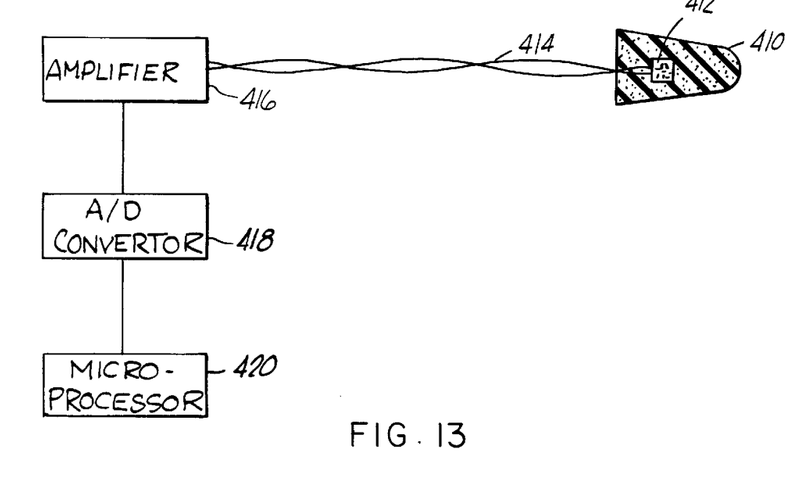
FIG. 13 is a partial block diagram illustrating yet another embodiment of the present invention utilizing an earpiece for monitoring an individual's blood pressure related parameters.

FIG. 13 illustrates yet another embodiment of the present invention. This embodiment differs from the previous embodiments in that instead of monitoring blood pressure and blood pressure related parameters by measuring air pressure changes in the earpiece wearer's sealed ear canal, this device monitors blood pressure and related parameters by detecting movement of the ear canal wall. This movement of the ear canal wall is transmitted via the material of earpiece 410, preferably a soft rubber, to a strain gauge means 412 provided in the earpiece, as shown. Strain gauge means 412 converts this transmitted movement into an electrical signal which is processed by circuitry similar to that shown in detail in FIG. 3. As shown more generally in FIG. 13, this signal is transmitted via lines 414 to an amplifier 416. Amplifier 416 amplifies the signal in a manner known to those skilled in the art and transmits it to an A/D converter 418 which converts the analog signal to a digital signal which is transmitted to microprocessor 420. Microprocessor 420 processes the signal so that it can be displayed, recorded, or otherwise processed as described earlier to enable one to monitor the wearer's blood pressure and the like.

This invention has been described in detail with reference to particular embodiments thereof, but it will be understood that various other modifications can be effected within the spirit and scope of this invention.

What is claimed is:

1. An apparatus for measuring blood pressure parameters comprising:
    an earpiece; and
    measuring means cooperating with said earpiece for measuring arterial blood pressure changes adjacent the ear canal.

2. An apparatus as claimed in claim 1 wherein said measuring means includes sensing means for measuring movement in the wall of an individual's ear canal which is caused by arterial blood pressure changes adjacent the ear canal.

3. An apparatus as claimed in claim 2 wherein said sensing means includes a strain gauge and wherein said strain gauge is built into said earpiece so as to be capable of measuring movement transmitted through said earpiece from the wall of the individual's ear canal.

4. An apparatus as claimed in claim 1 wherein said earpiece includes means for sealing an individuals ear canal so that arterial blood pressure changes adjacent the sealed ear canal produce air pressure changes in the sealed ear canal; and wherein said measuring means includes pressure sensing means for measuring the air pressure changes in the sealed ear canal.

5. An apparatus as claimed in claim 4 wherein said pressure sensing means is mounted in said earpiece.

6. An apparatus as claimed in claim 4 further comprising:
    means for adjusting the air pressure within the sealed ear canal.

7. An apparatus as claimed in claim 4 wherein said pressure sensing means produces a signal which is directly related to the measured air pressure changes.

8. An apparatus as claimed in claim 7 wherein the signal is an electrical signal.

9. An apparatus as claimed in claim 8 wherein the pressure sensing means is a member selected from the group consisting of piezoelectric transducers, strain gauges and ceramic transducers.

10. An apparatus as claimed in claim 7 wherein the signal is a mechanical signal.

11. An apparatus as claimed in claim 7 wherein the signal is a volumetric displacement.

12. An apparatus as claimed in claim 7 further comprising:
    means in communication with said pressure sensing means for displaying the signal produced by said pressure sensing means.

13. An apparatus as claimed in claim 7 further comprising:
    means in communication with said pressure sensing means for recording the signal produced by said pressure sensing means.

14. An apparatus as claimed in claim 7 further comprising:
    means for calibrating the signal with a reading produced by an independent blood pressure measuring means.

15. An apparatus as claimed in claim 7 further comprising:
    means in communication with said pressure sensing means for processing the signal produced by said pressure sensing means to monitor blood pressure parameters.

16. An apparatus as claimed in claim 15 wherein said processing means includes means for generating an audio signal which is directed to the sealed ear canal.

17. An apparatus as claimed in claim 16 wherein said means generates an audio signal when a predetermined blood pressure is detected.

18. An apparatus as claimed in claim 16 wherein all components thereof are built into said apparatus so that said apparatus is capable of being worn by an individual when said earpiece thereof is inserted into the individual's ear canal.

19. An apparatus as claimed in claim 18 further comprising housing means for containing battery means and said processing means.

20. An apparatus as claimed in claim 15 wherein the blood pressure parameters are selected from the group consisting of heart rate, systolic pressure, diastolic pressure, mean arterial pressure, continuous blood pressure waveform, stroke volume, cardiac output, respiration rate and respiration volume.

21. An apparatus as claimed in claim 15 further comprising:
    means for displaying the processed signal.

22. An apparatus as claimed in claim 15 further comprising:
    means for recording the processed signal.

23. An apparatus as claimed in claim 15 further comprising:
    transmitting means in communication with said pressure sensing means for transmitting the signal produced by said pressure sensing means to said processing means.

24. An apparatus as claimed in claim 23 wherein said transmitting means hard wired.

25. An apparatus as claimed in claim 23 wherein said transmitting means is wireless.

26. An apparatus as claimed in claim 25 wherein said wireless transmitting means includes a member selected from the group consisting of radio transmission means, ultrasonic transmission means, and photonic transmission means.

27. A system for measuring blood pressure comprising:

an earpiece for sealing an individual's ear canal;

pressure sensing means mounted in said earpiece for measuring air pressure changes in the ear canal when the ear canal is sealed with said earpiece wherein the air pressure changes are related to arterial blood pressure changes adjacent the ear canal, said pressure sensing means also producing a signal which is directly related to the measured air pressure changes;

auxiliary blood pressure measuring means for independently measuring a parameter of the individual's blood pressure, the measurement of which is used to calibrate the signal produced by said pressure sensing means;

processing means for processing the signal to measure blood pressure parameters; and transmitting means in communication with said pressure sensing means for transmitting the signal produced by said pressure sensing means to said processing means.

28. A system as claimed in claim 27 further comprising:

means for displaying the processed signal.

29. A system for measuring blood pressure parameters comprising:

earpiece means for sealing both ear canals of an individual so that arterial blood pressure changes adjacent each sealed ear canal produce air pressure changes in each sealed ear canal;

pressure sensing means for measuring the air pressure changes in each sealed ear canal and producing a signal for each sealed ear canal which is related to the measured air pressure changes; and processing means for processing and comparing the signals of each sealed ear canal to measure a blood pressure related parameter of the individual.

30. A system as claimed in claim 29 further comprising:

transmitting means in communication with said pressure sensing means for transmitting the signals produced by said pressure sensing means to said processing means.

31. A system as claimed in claim 29 wherein said processing means includes means for measuring the time delay between the signals.

32. A method of measuring blood pressure parameters comprising:

sealing an individual's ear canal so that arterial blood pressure changes adjacent the sealed ear canal produce air pressure changes in the sealed ear canal; and measuring the air pressure changes in the sealed ear canal.

33. A method as claimed in claim 32 further comprising:

producing a signal which is directly related to the measured air pressure changes.

34. A method as claimed in claim 33 further comprising:

displaying the signal.

35. A method as claimed in claim 33 further comprising:

recording the signal.

36. A method as claimed in claim 33 further comprising:

processing the signal to monitor a blood pressure parameter.

37. A method as claimed in claim 33 further comprising:

calibrating the signal with a reading produced by an independent blood pressure measuring means.

38. A method of measuring a blood pressure parameter comprising:

sealing both ear canals of an individual so that arterial blood pressure changes adjacent each sealed ear canal produce air pressure changes in each sealed ear canal;

measuring the air pressure changes in each sealed ear canal;

producing a signal for each sealed ear canal which is related to the measured air pressure changes; and comparing the signals of each sealed ear canal to measure a blood pressure related parameter of the individual.

39. A method as claimed in claim 38 wherein said step of comparing includes measuring the time delay between the signals.

40. A method of measuring blood pressure parameters comprising:

wearing an earpiece including means for measuring arterial blood pressure changes adjacent the ear canal; and measuring arterial blood pressure changes adjacent the ear canal with said earpiece.

* * * * *